(12) United States Patent
Bowersox, Jr. et al.

(10) Patent No.: US 6,393,926 B1
(45) Date of Patent: May 28, 2002

(54) FRONT-LOADING PRECISION MATERIAL SAMPLER WITH INTERCHANGEABLE RETRACTING CHAMBER

(75) Inventors: Clarence W. Bowersox, Jr.; Ivan V. Pinto, both of West Chester, PA (US)

(73) Assignee: Accutrol Co., Inc., West Chester, PA (US)

( * ) Notice: Subject to any disclaimer, the term of this patent is extended or adjusted under 35 U.S.C. 154(b) by 0 days.

(21) Appl. No.: 09/575,000

(22) Filed: May 19, 2000

(51) Int. Cl.[7] ................................................. G01N 1/12
(52) U.S. Cl. ................................. 73/864.64; 73/864.44
(58) Field of Search ........................ 73/863.33, 864.44, 73/864.45, 864.64, 864.16, 864.17, 864.18, 864.51, 864.53, 864.63

(56) References Cited

U.S. PATENT DOCUMENTS

| | | | |
|---|---|---|---|
| 176,038 A | 4/1876 | Nelson | |
| 455,733 A | 7/1891 | Bell | |
| 2,844,036 A | 7/1958 | Wright | |
| 3,042,124 A | * 7/1962 | Anderson | 175/20 |
| 3,080,760 A | 3/1963 | Piersma | |
| 3,266,323 A | * 8/1966 | Buchanan et al. | 73/864.62 |
| 3,444,938 A | * 5/1969 | Ballmann | 166/70 |
| 3,696,974 A | * 10/1972 | Van der Veken | 222/251 |
| 3,730,398 A | * 5/1973 | Goda | 222/309 |
| 3,732,735 A | * 5/1973 | Cohen | 73/425.6 |
| 4,023,716 A | 5/1977 | Shapiro | |
| 4,056,360 A | 11/1977 | Risch | |
| 4,116,247 A | * 9/1978 | Zanasi | 141/397 |
| 4,141,251 A | 2/1979 | Oshikubo | |
| 4,148,315 A | 4/1979 | Berezkin et al. | |
| 4,172,385 A | 10/1979 | Cristensen | |
| 4,359,110 A | * 11/1982 | Peterson | 175/20 |
| 4,433,587 A | 2/1984 | Risdal | |
| 4,840,517 A | 6/1989 | Bullivant | |
| 4,866,996 A | 9/1989 | Nohl et al. | |
| 5,272,926 A | 12/1993 | Wilkins | |
| 5,289,727 A | 3/1994 | Earle et al. | |
| 5,343,771 A | 9/1994 | Turriff et al. | |
| 5,476,017 A | 12/1995 | Pinto et al. | |
| 5,566,576 A | * 10/1996 | Sher et al. | 73/864.65 |
| 5,937,953 A | * 8/1999 | Melberg et al. | 175/20 |

FOREIGN PATENT DOCUMENTS

| | | |
|---|---|---|
| DE | 46450 | 3/1889 |
| EP | 0 259 260 A2 | 3/1988 |
| GB | 1 505 827 | 3/1978 |

OTHER PUBLICATIONS

Informational Brochure: " Introducing Accu–Sampler™ for Blend Sampling of Powders & Granulations"; Date and author unknown; one double–sided page.

* cited by examiner

Primary Examiner—Hezron Williams
Assistant Examiner—Charles D. Garber
(74) Attorney, Agent, or Firm—Ratner & Prestia

(57) ABSTRACT

A bulk material sampler comprising an elongated body having a first axial bore and an interior wall, a handle having a second axial bore and a finger grip, and a shaft assembly axially supported. inside the first and second bores. The bottom end of the handle is connected to the top end of the body. The shaft assembly comprises a tip at the shaft assembly bottom end and a button at the shaft assembly top end. The button is adapted to protrude from the handle top end. The shaft assembly is axially moveable between an actuated position in which the button is maximally depressed within the handle, and a resting position in which the button maximally protrudes from the handle. The sampler further comprises means for biasing the shaft in the resting position, and a sample collection cavity defined by a portion of the tip and a portion of the body interior wall. The tip may be removable from the shaft assembly. A plurality of tips having different configurations tailored for sampling different bulk materials are claimed, as are methods for taking a sample using the sampler.

16 Claims, 3 Drawing Sheets

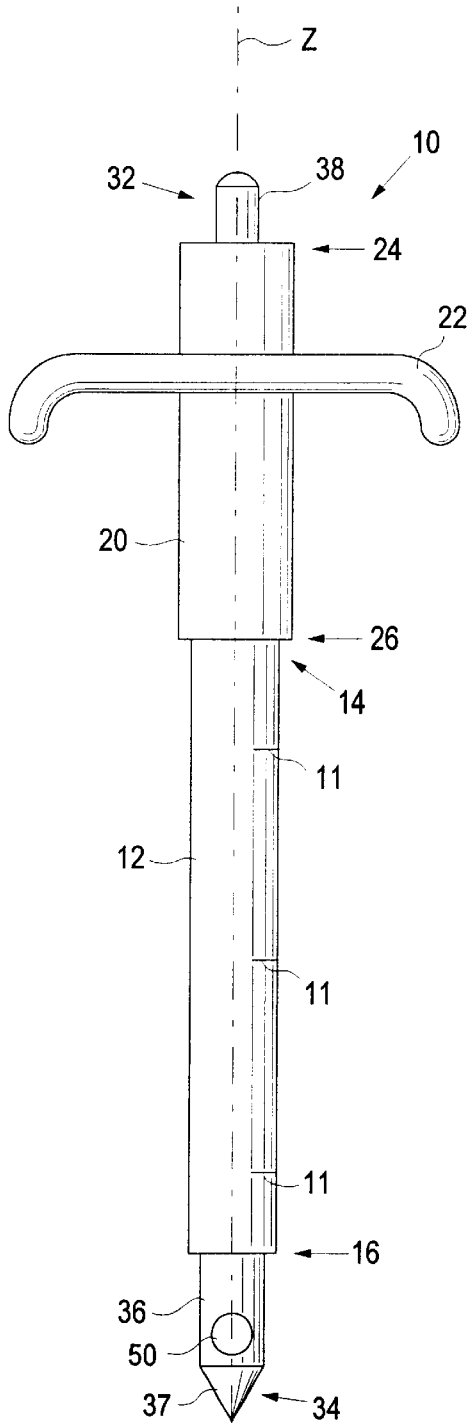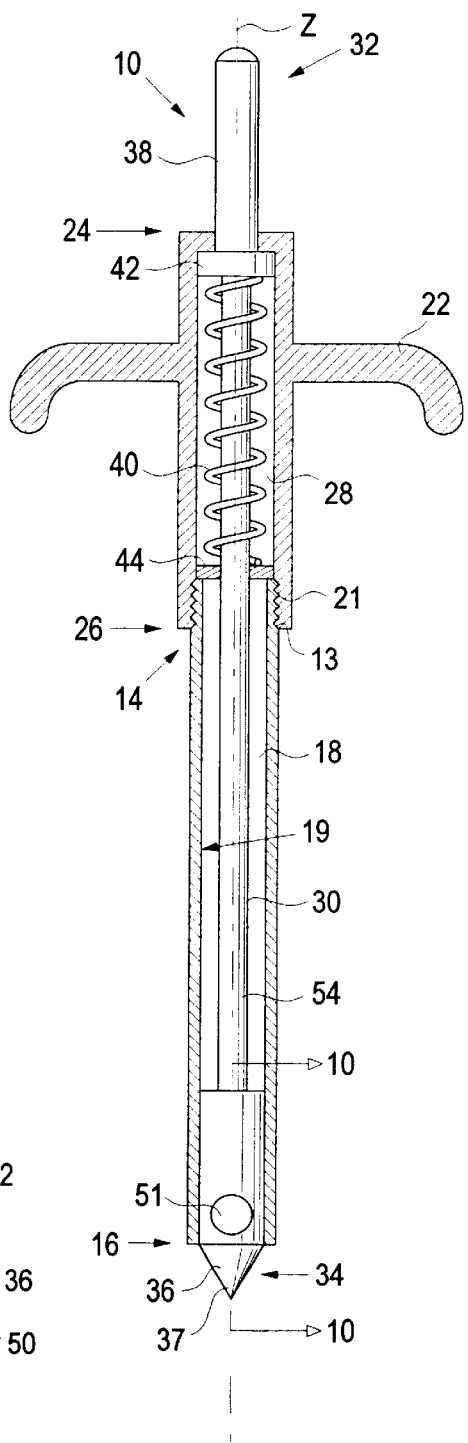
FIG. 1          FIG. 10          FIG. 2

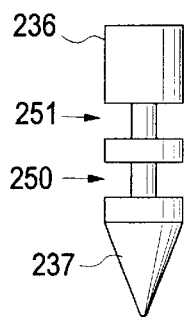
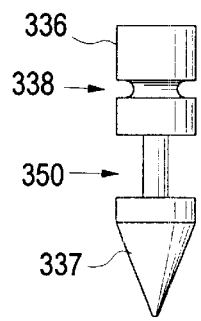
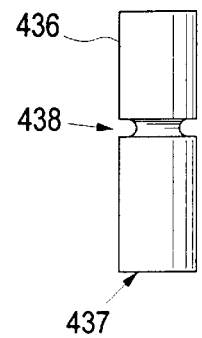
FIG. 5        FIG. 6        FIG. 7
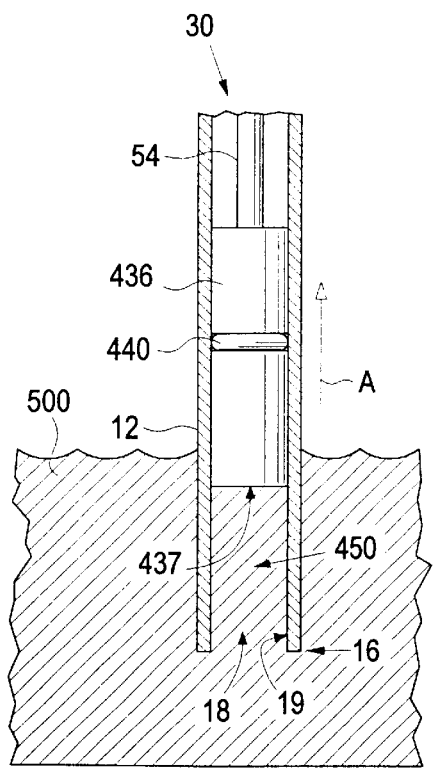
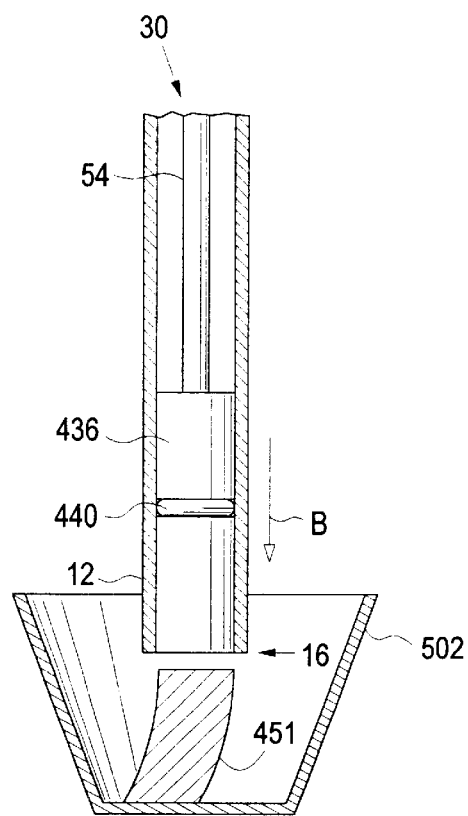
FIG. 8        FIG. 9

FRONT-LOADING PRECISION MATERIAL SAMPLER WITH INTERCHANGEABLE RETRACTING CHAMBER

TECHNICAL FIELD

The present invention relates generally apparatus for sampling of solid, liquid, and semi-solid bulk materials such as powders, liquids, and gels, and more specifically, to a non-compacting bulk material sampler.

BACKGROUND OF THE INVENTION

Sampling of bulk mixtures of granular or powdery materials to evaluate the degree of mixing at different locations in a mixing vessel is typically done using a probe or sample "thief" that is inserted in the bulk mixture to remove a representative sample. A typical sample thief comprises a long tubular shell having at least one aperture on a side wall near the lower end of the probe, and a second inner mating tube also having at least one aperture. The aperture in the inner tube can be aligned with the aperture in the outer tube by rotating the inner tube within the outer tube. In operation, the probe is inserted in the bulk mixture to the desired depth with the inner tube and outer tube apertures not aligned. After insertion of the tube to a desired depth, the inner tube is rotated to aligri the two openings, thus allowing bulk material to flow in the opened inner tube. The opening is then closed by again rotating the inner tube, and the probe is removed from the bulk material thus retrieving a sample of the material from a desired point in the mixing vessel. The sample retrieved is then recovered from the probe by re-aligning the inner and outer tube apertures and allowing the sample to fall out into a sample container, from which the sample then can be processed for further analysis or study as needed.

Sampling of bulk materials in a precise, repeatable and reproducible manner has historically been a technical challenge not readily overcome. For example, the mere rotation of the inner tube within the outer tube does not necessarily provide an impetus to draw the sample into the apertures. Thus, shaking or other movement may be required. Furthermore the rotation motion is not easily accomplished with one hand. Sometimes it is desired to use a single sample thief with a number of mating apertures in the inner and outer tubes for taking samples at a number of depths simultaneously. To allow for the rotation between the inner and outer tubes, there is necessarily a certain degree of tolerance between inner and outer tubes. The shaking motion necessary to draw sample into the apertures may also cause some of the sample collected through an upper set of apertures to fall between the inner and outer tubes into the sample collected at a lower set of apertures. This contamination of the sample from one depth with the sample from another may be undesirable.

Samplers are known that are particularly adept at overcoming many of these problems, such as for example, the samplers described in U.S. Pat. Nos. 5,476,017 and 5,703,301, assigned to the common assignee of this invention. These samplers, however, provide compacting of the sample, which is desirable in many applications. In other applications, however, it may be desired not to compact the sample. In still other applications, it may be desirable to have a sampler capable of not only sampling bulk powder or granular material, but also liquid or gelatinous material.

Thus, non-compacting sampling apparatus are still desired that are able to recover predetermined size samples from mixing bulk materials with a high degree of repeatability of the sample size, with minimal disturbance of the bulk material in the sampling vicinity, and with the ability to recover substantially all of the retrieved sample from the sampling apparatus in a format easily amenable to further testing. It is further desirable to provide such apparatus that are maneuverable with one hand and that are adaptable for use in a multitude of applications.

SUMMARY OF THE INVENTION

The invention comprises a bulk material sampler comprising an elongated body, a handle, and a shaft assembly. The body has an axis, a first axial bore, and an interior wall; the handle is coaxial with the body axis and has a second axial bore and a finger grip. The bottom end of the handle is connected to the top end of the body. The shaft assembly is supported in the first and second bores coaxial with the body axis. The shaft assembly comprises a tip at the shaft assembly bottom end and a button at the shaft assembly top end. The button is adapted to protrude from the handle top end. The shaft assembly is axially moveable between an actuated position in which the button is maximally depressed within the handle, and a resting position in which the button maximally protrudes from the handle. The comprises means for biasing the shaft in the resting position and a sample collection chamber defined by a portion of the tip and a portion of the body interior wall.

The tip may comprise a sample collection cavity therein, and may be adapted to at least partially protrude from the body bottom end such that the tip maximally protrudes in the actuated position and minimally protrudes in the resting position. The sample collection cavity in the tip may, for example, comprise an annular cutout coaxial with the body axis or a bore hole perpendicular to the body axis.

The tip may be removable from the shaft assembly. A number of tip configurations may be provided, each tailored for particular sampling applications. For example, a tip adapted for bulk powder sampling may comprise a pointed endpiece adapted to protrude from the body even in the resting position. A tip having a plurality of sample collection cavities axially spaced from one another may be adapted for taking multiple samples. A tip adapted for liquid sampling may comprise a groove above the sample collection cavity and an o-ring in the groove. A tip adapted for sampling of gelatinous materials may comprise a blunt bottom end, a groove, and an o-ring in the groove, in which the tip bottom end is adapted to be substantially flush with the body bottom end when the shaft assembly is in the actuated position and maximally receded when the shaft assembly is in the resting position. With the gel-sampling tip attached, the sample collection chamber is defined by the body interior wall between the bottom end of the tip and the bottom end of the body when the shaft is in the resting position.

In one embodiment, the invention comprises a sampler for bulk solid material comprising a first elongated outer sleeve, a second elongated coaxial inner member moveably nestled in the outer sleeve, means for extending an end portion of the inner member from a first axial position within the outer sleeve to a second axial position outside the outer sleeve; and non-compacting means in the inner member end portion for collecting bulk solid material in the end portion when said sampler is inserted in the bulk solid material. The inner member end portion may comprise a cavity at a lower end thereof for collecting bulk solid material when the sampler is inserted in the bulk solid material.

BRIEF DESCRIPTION OF DRAWING

The invention is best understood from the following detailed description when read in connection with the accompanying drawing. It is emphasized that, according to common practice, the various features of the drawing are not to scale. On the contrary, the dimensions of the various features are arbitrarily expanded or reduced for clarity. Included in the drawing are the following figures:

FIG. 1 is a side view of an exemplary sampler of this invention in the actuated position.

FIG. 2 is a cross-sectional side view of the sampler of FIG. 1.

FIG. 5 is an exemplary removable designed tip for taking multiple samples.

FIG. 6 is an exemplary removable tip designed for taking liqud samples.

FIG. 7 is an exemplary removable tip designed for taking samples of geatinous materials.

FIG. 8 is a partial cross section of an exemplary sampler outfitted with the tip of FIG. 7 in the relaxed position after taking a sample.

FIG. 9 is a partial cross section of an exemplary sampler outfitted with the tip of FIG. 7 in the actuated position after expelling a sample.

FIG. 10 is cross section taken across line 10—10 of the removable tip shown in FIG. 9.

DETAILED DESCRIPTION OF INVENTION

Figures 3, 4:
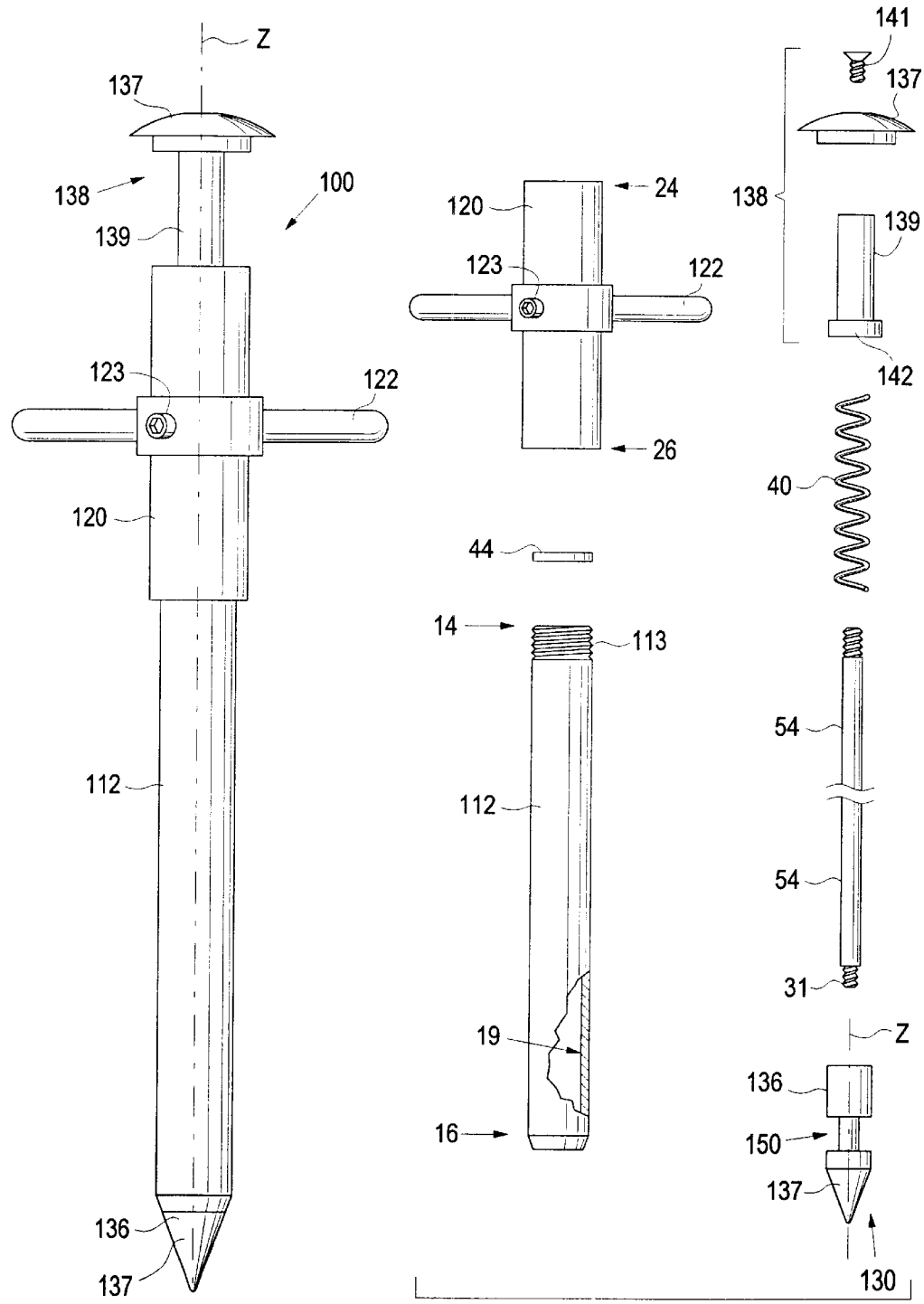
FIG. 3 is a side view of another exemplary sampler of this invention in the resting position.
FIG. 4 is an exploded view of the sampler of FIG. 3.

Referring now to the drawing, wherein like reference numerals refer to like elements throughout, FIGS. 1 and 2 show an exemplary bulk material sampler 10 of this invention. The sampler outwardly comprises an elongated body 12 having a top end 14 and a bottom end 16, and a handle 20 having a finger grip 22, a top end 24, and a bottom end 26. Handle bottom end 26 is connected to body top end 14. Body 12 comprises a first axial bore 18 therethrough along body axis Z, forming body interior wall 19. Handle 20 comprises a second axial bore 28 also along body axis Z. Thus, body 12 and handle 20 together form an elongated outer sleeve.

Shaft assembly 30 is supported within the first bore 18 and second bore 28 coaxial with body axis Z. Shaft assembly 30 has a top end 32 and a bottom end 34, comprising a tip 36 at the bottom end and a button 38 at the top end. Button 38 is adapted to protrude from top end 24 of handle 20. Shaft assembly 30 is axially moveable between an actuated position as shown in FIG. 1 in which button 38 is maximally depressed within handle 20, and a resting position as shown in FIG. 2 in which the button maximally protrudes from the handle. The sampler comprises means for biasing the shaft assembly in the resting position, such as spring 40 compressed between bottom lip 42 of button 38 and annular top piece 44 attached to body 12, as shown in FIG. 2.

As shown in FIGS. 1, 2, and 10, tip 36 comprises a sample collection cavity 50 therein. Thus, a sample collection chamber 51 is defined by sample collection cavity 50 in tip 36 and interior wall 19 of body 12. Tip 36 is adapted to protrude at least partially from bottom end 16 of body 12 even when shaft assembly 30 is in the resting position. Tip 36 maximally protrudes when shaft assembly 30 is in the actuated position, as shown in FIG. 1, and minimally protrudes when the shaft assembly is in the resting position, as shown in FIG. 2. As shown in FIG. 10, sample collection cavity 50 of tip 36 comprises a bore hole perpendicular to body axis Z. Tip 36 has a conical pointed endpiece 37. Also, as shownin FIG. 10, tip 36 comprises female threads 52 adapted for receiving mating male threads (not shown) at the bottom of shaft 54 of shaft assembly 30.

Another exemplary sampler 100 is shown in FIGS. 3 and 4. This sampler also has a body 112, handle 120, sample tip 136 and button assembly 138 as shown in FIG. 3. Sampler 100 has an axially adjustable finger grip 122 that can be moved up and down and set in a preferred position using set screw 123. Button assembly 138 comprises palm knob 137, button stem 139, and flathead screw 141. Palm knob 137 is adapted to comfortably conform to the shape of a standard user's palm (not shown), and is attached to button stem 139 with flathead screw 141. Tip 136 comprises an annular cutout 150 coaxial with body axis Z and a pointed endpiece 137 adapted to protrude from body 12 even in the resting position, as shown in FIG. 3. Spring 40 is compressed between lip 142 of button stem 138 and annular top piece 44 which may, for example, simply be a washer or nut that is welded or otherwise attached to top end 14 of body 112. Bottom end 16 of body 112 is chamfered, as shown in FIG. 4, providing a smooth transition between bottom end 16 of body 112 and pointed endpiece 137 of tip 136.

Shaft assembly 130 comprises tip 136, shaft 54, button stem 139, button knob 137, and flat head screw 141, as shown vertically aligned in FIG. 4. Shaft 54 is shown with male threads 31 for connecting to female threads in tip 136 (the female threads are not shown in FIG. 4, but are similar to those shown in FIG. 10). It should be understood that, conversely, the female threads may be on the shaft and the male threads may be on the tip, or that other means for connecting the tip and the shaft may also be used, such as a quick connect fitting, many examples of which are known in the art. Shaft 54 is also shown with male threads for connecting the shaft to button stem 138, which has a lower set of mating female threads (not shown). Button stem also has an upper set of female threads (not shown) for receiving flathead screw 141.

Body 112 has external male threads 113 at top end 14. Threads 113 mate with female threads in handle 120 (not shown in FIG. 4, but similar to threads 21 in handle 20 that mate with male threads of body 12, as shown in FIG. 2). 11. This threaded connection between body 112 and handle 120 provide tip 136 with an adjustable axial position relative to the body. As threads 113 are tightened further into handle 120, tip 136 protrudes axially further from the body in both the resting and actuated positions.

Tips 36 and 136 are designed for sampling bulk powders. Pointed endpieces 37 and 137 provide mechanical advantage in inserting the sampler and in pushing the column of powder out of the way when moving the sampler from the resting to the actuated position to take the sample. Although the mechanical advantage provided by pointed endpiece 37 or 137 is desirable, it is not critical, and thus the endpiece may be blunt, rounded, or even concave. The downward movement of tip 36 or 136 when the shaft assembly is moved from the resting to the actuated position creates movement within the powder that facilitates the powder filling the sample collection cavity 50 or 150. Once the sample fills sample collection cavity 50 or 150, the tip is retracted into body 12 or 112 again. The sample is then confined within a sample collection chamber defined by sample collection cavity 50 or 150 and the interior wall 19 of body 12 or 112 until the sampler is actuated again, preferably above a sample container to receive the sample that is expelled.

Tip 36 provides an advantage over typical rotating inner and outer tube thieves of the prior art because the geometry of pointed endpiece 37 and the downward motion of shaft assembly 30 from the resting position to the actuated position provides movement within the bulk material that facilitates filling collection cavity 50. Tip 136 provides an even greater advantage over the prior art. Because sample collection cavity 150 is an annular cutout in tip 136 coincident with body axis Z of the sampler, the bulk material needs to travel less distance and into a less confining space to fill annular sample collection cavity 150 of tip 136 than bore hole sample collection cavity 50 of tip 36.

Referring now to FIG. 5, a tip 236 may be provided with multiple sample collection cavities 250 and 251. Such multiple cavities may be desired if there is a need to provide redundant samples of a specific cavity of the bulk material. The individual samples may then be expelled from the sampler into a sample container by first only partially actuating the sampler so that only the first cavity 250 empties. Then the sampler can be placed above a second sample container and actuated the remaining amount so that the second cavity 251 empties. Although shown only with 2 sample collection cavities in FIG. 5, more than 2 such cavities may be provided. Although shown with the annular cutout type of sample collection cavity in FIG. 5. multiple perpendicular bore hole type sample collection cavities similar to cavity 50 shown in FIGS. 1, 2, and 10 may also be provided. As tip 236 is still designed for powder sampling, the tip optimally has a pointed endpiece 237.

Other tip designs may be particularly well-suited for sampling liquids or gels. Referring now to FIG. 6, there is shown tip 336 designed for taking liquid samples. Above the sample collection cavity 350, tip 336 comprises a groove 338 adapted to fit an o-ring (not shown in FIG. 6, but similar to o-ring 440 shown in FIGS. 8 and 9). The o-ring is adapted to provide a seal between tip 336 and the body (not shown) such that movement of the shaft (not shown) between the actuated and resting positions creates a vacuum that assists in drawing a liquid sample into sample collection cavity 350. Although shown with a pointed endpiece 337, the pointed endpiece provides little incremental advantage when sampling liquids than when sampling powders.

Referring now to FIGS. 7–9 there is shown a tip 436 designed for taking samples of highly viscous materials such as gels or ointments that require additional impetus to fill a sample chamber with material. Tip 436 comprises a blunt bottom end 437, a groove 438, and an o-ring 440 in the groove. Bottom end 437 of tip 436 is adapted to be substantially flash with bottom end 16 of body 12 in the actuated position as shown in FIG. 9 and maximally receded in the resting position as shown in FIG. 8. Sample collection chamber 450 comprises the cavity defined by interior wall 19 of body 12 between bottom end 437 of the tip and bottom end 16 of the body. o-ring 440 provides a seal between tip 436 and the body 12 such that retraction of shaft 54 from the actuated position to the resting position creates a vacuum that assists in drawing in and retaining a gelatinous sample 451 in the sample collection chamber.

To take samples of powders and liquids, the sampler is typically inserted into the material in the resting position until the tip is at the desired depth. To assist in assuring that the sampler tip is at a proper depth, the body may comprise one or more depth markings 11 (shown in FIG. 1) for indicating a predetermined depth of the sampler when immersed in a sample container up to the depth marking. Then the button is pushed so that the shaft assembly is in the actuated position, during which time the powder or liquid fills the sample collection cavity. The shaft assembly is then allowed to return to the resting position so that the sample is protected within the sample collection cavity inside the body, and the sampler is withdrawn. To expel the sample into an appropriate container, the sampler is held above the container and the shaft assembly moved again into the actuated position until the sample is discharged. Depending on the properties of the sampled material, a light tap may be necessary to dislodge the sample. The entire sampling procedure may be accomplished using only one hand, particularly using only one hand to move the shaft assembly between the resting and actuated positions, unlike standard samplers in the art.

To take samples of gelatinous material, the sampler is operated in a somewhat opposite way than for powders and liquids. For gelatinous materials 500, such as shown in FIG. 8, the sampler button (not shown) is pushed in so that the shaft assembly is in the actuated position (shown in FIG. 9) during insertion into the gel. This prevents gelatinous material from filling sample collection chamber 450 during insertion of the probe, assuring that the cavity from which the sample is collected is at the desired depth. When the tip reaches the desired depth, shaft assembly 30 is moved into the resting position along arrow A as shown in FIG. 8, thus drawing the sample into sample collection chamber 450. Some pulling force on the button may be required to return the sampler to the resting position, depending on the thickness of the gel. To maintain single hand operation, however, the spring that biases the shaft assembly in the resting position may be designed to exert sufficient force to overcome the viscosity and cohesiveness of the gel and to pull a sample into the chamber without additional force needed. Then, the sampler is removed from the bulk material, shaft assembly 30 is returned to the actuated position along arrow B by pushing the button (not shown), and sample 451 is expelled from sample collection chamber 450 into collection container 502. Although a sample from the top layer of gelatinous material can be taken merely by inserting the sampler into the material with the shaft assembly in the resting position, insertion in the actuated position is recommended to assure that a full sample is collected. Otherwise, the user risks capturing only a partial sample due to trapped air in the sample collection chamber.

It should be understood that although it is desirable for the sampler to have removable tips to provide a single sampler assembly that can be used to sample multiple types of materials, a sampler having only a single tip permanently attached may also be provided. In addition to the different types of sample tips optimally designed for different types of bulk materials, multiple tips of the same general design but having sampling cavitys of different volumes may also be provided. The removable tips may be provided along with a sampler, or may be provided for sale separately.

To replace a tip, for example in sampler 100 shown in FIGS. 3 and 4, handle 120 and body 112 are first unscrewed and shaft assembly 130 is drawn upwardly until shaft 54 can be gripped, such as with pliers. Button assembly 138 is then unscrewed from shaft 54 and the shaft is removed through bottom end 16 of body 112. Tip 136 can then be removed from shaft 54 and the desired replacement tip substituted. The above steps are then reversed to reassemble the sampler. A similar process may be followed for sample 10, shown in FIGS. 1 and 2. The easy disassembly of the components is also desirable for easy cleaning of the sampler.

The sampler of this invention is particularly useful for sampling solid, liquid, and semi-solid bulk materials such as active and inactive or inert ingredients used in chemical, food, pharmaceutical, cosmetic, ceramic, metallurgical, geological, and soil technologies, or in any industry where bulk material sampling is useful for process control or product quality assurance. The usefulness of this sampler is not limited to any of the above fields or types of materials, however. Any materials of construction are suitable for the sampler, and are dictated by the end use. For example, in applications where disposable samplers are desired, inexpensive plastics or resins may be used. For standard pharmaceutical and food applications, components of stainless steel, brass, or combinations thereof may be desired. For unusually corrosive atmospheres, more exotic materials may be necessary. The invention is not limited to any particular type of materials.

Although a coil spring means is shown for biasing the sampler in the actuated position between lower lip 42 of button 38 or lower lip 142 of button stem 139 and annular top piece 44, any other means known in the art may be used. In particular, structures known in the art of pushbutton retractable ballpoint pen manufacture may be employed in the design of a sampler according to this invention. Accordingly, numerous variations are available on the placement of the spring, the stops between which the spring is compressed on the shaft assembly and on the body, and the structure of the button stem. For example, the button stem may comprise a cam that moves in relation to one or more structures that protrude from the interior wall of the axial bore in the handle to provide functionality similar to a pushbutton retractable pen. Such pens are known in the art for the ability of the user to push the button with one "click" to maneuver the pen tip into a fixed extended position for writing and then to push the button again to retract the tip for storage. A multitude of designs are available to provide this functionality, all of which may be suitable means for biasing the sampler of this invention in the actuated position, but none of which are detailed here, as such designs are well known and documented in the art. Traditionally, such pens also have a super-actuated position during each click in which the tip is extended slightly further than in the actuated position. A sampler conforming to such a design may also have such a superactuated position.

Although shown with a single piece, rounded end button 38 in FIGS. 1 and 2 and with a multi-piece button assembly 138 in FIGS. 3 and 4, the button design is not limited to those examples. Other button designs may be used without departing from the spirit of the invention. The same is true for the other components of the sampler. Although illustrated and described above with reference to certain specific embodiments, the present invention is nevertheless not intended to be limited to the details shown. Rather, various modifications may be made in the details within the scope and range of equivalents of the claims and without departing from the spirit of the invention.

What is claimed:

1. A bulk material sampler comprising:
   an elongated body having a top end, a bottom end, an axis, and a first axial bore therethrough, and an interior wall;
   handle coaxial with the body axis and having a second axial bore, a finger grip, a top end, and a bottom end, the handle bottom end connected to the body top end;
   a shaft assembly supported in the first and second bores coaxial with the body axis and having a top end and a bottom end, said shaft assembly comprising a removable tip at the shaft assembly bottom end and a button at the shaft assembly top end, the removable tip comprising a first threaded interface for attachment to a mating threaded interface on the shaft assembly, the button adapted to protrude from the handle top end, and the shaft assembly being axially moveable between a fully actuated position in which the button is maximally depressed within the handle and a resting position in which the button maximally protrudes from the handle, the tip having a fully actuated axial location relative to the body when the shaft assembly is in the fully actuated position, wherein the tip fully-actuated axial location is adjustable relative to the body;
   means for biasing the shaft in the resting position; and
   a sample collection chamber defined by a portion of the tip and a portion of the interior wall of the body.

2. The sampler of claim 1 wherein the tip further comprises a sample collection cavity that defines a portion of the sample collection chamber.

3. The sampler of claim 2 wherein the sample collection cavity comprises an annular cutout in the tip coaxial with the body axis.

4. The sampler of claim 2 wherein the sample collection cavity comprises a bore hole in the tip perpendicular to the body axis.

5. The sampler of claim 2 wherein the tip further comprises a plurality of sample collection cavities axially spaced from one another.

6. The sampler of claim 5 wherein each sample collection cavity comprises an annular cutout in the tip coaxial with the body axis.

7. The sampler of claim 2 wherein the tip further comprises a groove above the sample collection cavity and an o-ring in the groove, the o-ring adapted to provide a seal between the tip and the body such that movement of the shaft between the actuated and resting positions creates a vacuum that assists in drawing a liquid sample into the sample collection cavity.

8. The sampler of claim 1 wherein the tip is adapted to at least partially protrude from the body bottom end such that the tip maximally protrudes when the shaft assembly is in the actuated position and minimally protrudes when the shaft assembly is in the resting position.

9. The sampler of claim 8 wherein the tip comprises a pointed endpiece.

10. The sampler of claim 1 wherein the tip comprises a blunt bottom end, a groove, and an o-ring in the groove, and in which the tip bottom end is adapted to be substantially flush with or protruding from the body bottom and in the actuated position and maximally receded in the resting position, such that the sample collection chamber is defined by the body interior wall between the bottom end of the tip and the bottom end of the body when the shaft assembly is in the resting position, the o-ring adapted to provide a seal between the tip and the body such that retraction of the shaft assembly from the actuated to the resting position creates a vacuum that assists in drawing in and retaining a gelatinous sample in the sample collection chamber.

11. The sampler of claim 1 wherein the means for biasing the shaft in the resting position comprises a spring.

12. The sampler of claim 1 comprising an adjustable connection between the handle and the body that controls the fully actuated axial position of the tip.

13. The sampler of claim 12, wherein the adjustable connection comprises a threaded connection between the handle and the body.

14. The sampler of claim 1 wherein the body comprises one or more depth markings for indicating a predetermined depth of the tip when immersed in a material to be sampled up to the depth marking.

15. The sampler of claim 1 wherein the first threaded interface comprises female threads and the mating threaded interface comprises male threads.

16. A bulk material sampler comprising:

an elongated body having a top end, a bottom end, an axis, and a first axial bore therethrough, and an interior wall;

a handle coaxial with the body axis and having a second axial bore, a finger grip having an axial position that is adjustable relative to the handle, a top end, and a bottom end, the handle bottom end connected to the body top end;

a shaft assembly supported in the first and second bores coaxial with the body axis and having a top end and a bottom end, said shaft assembly comprising a removable tip at the shaft assembly bottom end and a button at the shaft assembly top end, the removable tip comprising a first threaded interface for attachment to a mating threaded interface on the shaft assembly, the button adapted to protrude from the handle top end, and the shaft assembly being axially moveable between a fully actuated position in which the button is maximally depressed within the handle and a resting position in which the button maximally protrudes from the handle;

means for biasing the shaft in the resting position; and a sample collection chamber defined by a portion of the tip and a portion of the interior wall of the body.

* * * * *

UNITED STATES PATENT AND TRADEMARK OFFICE
CERTIFICATE OF CORRECTION

PATENT NO. : 6,393,926 B1
DATED : May 28, 2002
INVENTOR(S) : Bowersox, Jr. et al.

It is certified that error appears in the above-identified patent and that said Letters Patent is hereby corrected as shown below:

Column 1,
Line 27, delete "aligri" and insert therefore -- align --;

Column 2,
Line 22, after the word "The" and before the word "comprises", insert -- sampler --;

Column 3,
Line 18, delete "geatinous" and insert therefore -- gelatinous --;

Column 4,
Line 1, delete "shownin" and insert therefore -- shown in --;

Column 5,
Line 52, delete "o-ring" and insert therefore -- O-ring --.

Column 8,
Line 43, delete "and" and insert therefore -- end --.

Signed and Sealed this

Thirty-first Day of December, 2002

JAMES E. ROGAN
*Director of the United States Patent and Trademark Office*